US005670146A

United States Patent [19]

Welte et al.

[11] Patent Number: 5,670,146
[45] Date of Patent: *Sep. 23, 1997

[54] PHARMACOLOGICAL PREPARATIONS COMPRISING HUMAN PLURIPOTENT HEMATOPOIETIC COLONY STIMULATING FACTOR

[75] Inventors: Karl Welte, New York, N.Y.; Erich Platzer, Erlangen, Germany; Janice L. Gabrilove, New York, N.Y.; Roland Mertelsm, Chappaqua, N.Y.; Malcolm A. S. Moore, Larchmont, N.Y.

[73] Assignee: Sloan-Kettering Institute, New York, N.Y.

[*] Notice: The term of this patent shall not extend beyond the expiration date of Pat. No. 5,532,341.

[21] Appl. No.: 480,356

[22] Filed: Jun. 7, 1995

Related U.S. Application Data

[63] Continuation of Ser. No. 280,582, Jul. 26, 1994, Pat. No. 5,532,341, which is a continuation of Ser. No. 132,240, Oct. 6, 1993, abandoned, which is a continuation of Ser. No. 835,270, Mar. 7, 1986, abandoned, which is a continuation-in-part of Ser. No. 716,844, Mar. 28, 1985, abandoned.

[51] Int. Cl.$^6$ .............................. A61K 38/19; C07K 14/53
[52] U.S. Cl. ........................ 424/85.1; 530/351; 530/350; 530/395; 435/69.5; 435/69.1
[58] Field of Search ................................ 530/351, 350, 530/395; 424/85.1; 435/69.5, 69.1

[56] References Cited

U.S. PATENT DOCUMENTS

| | | | |
|---|---|---|---|
| 4,621,050 | 11/1986 | Sugimoto et al. | 435/70.2 |
| 4,810,643 | 3/1989 | Souza | 435/69.5 |
| 5,043,156 | 8/1991 | Matsumoto et al. | 424/85.1 |
| 5,532,341 | 7/1996 | Welte et al. | 530/351 |

FOREIGN PATENT DOCUMENTS

| | | |
|---|---|---|
| 0 169 566 | 1/1986 | European Pat. Off. . |
| 8 604 506 | 8/1986 | Japan . |

OTHER PUBLICATIONS

Platzer, E., et al., Biological Characterization of Human Pluripotent Colony–Stimulating Factor (abstract).
Welte, K., et al., Purification and Biochemical Characterization Human Pluripotent Hematopoietic Colony–Stimulating Factor produced by Human Bladder Carcinoma Cell Line (abstract).
Metcalf, Hemopoietic Colonies, ed. Metcalf, Springer–Verlag, New York, pp. 9, 4, 200 (1977).
Nicola, N.A., et al., Blood 54 (3): 614–627 (1979).
Lusis et al., Blood 57: 13–21 (1981).
Abdoud et al., Blood 58 (6): 1150–1154 (1981).
Morstyn, G., et al., J.Cell. Physiol. 109: 133–142 (1981).
Wu, M.-C., et al., J. Clin. Invest. 67: 1588–1591 (1981).
Moore, M.A.S., J. Cell. Physiol. Supplement, vol. 1: 53–64 (1982).
Okabe et al., J. Cell. Physiol. 110: 43–47 (1982).
Metcalf et al., J. Cell. Physiol. 116: 198–206 (1983).
Nicola, N.A., et al., J. Biol. Chem. 258 (14): 9017–9023 (Jul. 25, 1983).
Vadas, M.A., et al., J. Immunol. 130 (2): 795–799 (Feb. 1983).
Clark, Lewis, J. Biol. Chem. 259: 7488–7492 (1984).
Dexler, Nature 309: 746–747 (1984).
Gasson, J.C., et al., Science 226: 1339–1342 (1984).
Nathan, C.F., et al., J. Exp. Med. 160: 600–605 (1984).
Tsuneoka et al., Cell Structure and Function 9: 67–81 (1984).
Gabrilove et al., Blood 66: 407–415 (Aug. 1985).
Moore, M.A.S., et al., in Mediators in Cell Growth and Differentiation, vol. 37 pp. 147–158 (1985).
Nicola, N.A., et al., Nature 314: 625–628 (Apr. 18, 1985).
Nicola, N.A., et al., J. Cell. Physiol. 124: 313–321 (1985).
Nicola, N.a., Methods in Enzymology 116: 600–619 (1985).
Platzer, E., et al., Modern Trends in Human Leukemia VI, Springer—Verlag, Neth at al. (Eds.) pp. 418–422 (1985).
Platzer, E., et al., J. Exp. Med. 162: 1788–1801 (Dec. 1985).
Welte, K., et al., Modern Trends in Human Leukemia VI, Springer–Verlag, Neth. et al. (Eds.) pp. 398–401 (1985).
Welte, K., et al., Proc. Natl. Acad. Sci., USA 82: 1526–1530 (Mar. 1985).
Nagata, S., et al., Nature 319:415–418 (Jan. 30, 1986).
Nagata, s., et al., The EMBO Journal 5 (3): 575–581 (1986).
Nomura, H., et al., The EMBO Journal 5 (5): 871–876 (1986).

*Primary Examiner*—Vasu S. Jagannathan
*Assistant Examiner*—Elizabeth C. Kemmerer
*Attorney, Agent, or Firm*—Bell, Boyd & Lloyd

[57] ABSTRACT

Highly purified Pluripotent hematopoietic colony-stimulating factor (pluripotent CSF), a glycoprotein (MW 19,600) constitutively produced by human tumor cells has been highly purified from low serum-containing conditioned medium to apparant homogeneity. Pluripotent CSF supports the growth of human mixed colonies (CFU-GEMM), granulocyte-macrophage colonies (CFU-GM), early erythroid colonies (BFU-E) and induces differentiation of human leukemic cells. The specific activity of the purified pluripotent CSF in the CFU-GM assay is $1.5 \times 10^8$ U/mg protein.

10 Claims, 6 Drawing Sheets

PHARMACOLOGICAL PREPARATIONS COMPRISING HUMAN PLURIPOTENT HEMATOPOIETIC COLONY STIMULATING FACTOR

This application is a continuation of Ser. No. 08/280,582, filed Jul. 26, 1994, now U.S. Pat. No. 5,532,341, which is a continuation of Ser. No. 08/132,240, filed Oct. 6, 1993, now abandoned, which is a continuation of Ser. No. 06/835,270, filed Mar. 7, 1986, now abandoned, which is a continuation-in-part of Ser. No. 06/716,844, filed Mar. 28, 1985, now abandoned.

This work was done in part with government funding under United States Public Health Service Grants CA-32516, HL-31780, CA-20194, CA-23766 and CA-00966. Therefore the government has certain rights in this invention.

This application concerns human pluripotent colony stimulating factor (P-CSF) also known as pluripoietin.

BACKGROUND

Abbreviations

CFU-GEMM: Colony forming unit—granulocyte, erythroid, macrophage, megakaryocyte.

CFU-GM: Colony forming unit—granulocyte-macrophage

BFU-E: erythroid burst forming unit

GM-CSF: Granulocyte-macrophage colony stimulating factor

Colony-stimulating factors (CSFs) are hormone-like glycoproteins produced by a variety of tissues and tumor cell lines which regulate hematopoiesis and are required for the clonal growth and maturation of normal bone marrow cell precursors in vitro (Burgess, A. W., et al. (1980) Blood 56: 947–958; Nicola, N. A., et al. (1984) Immunology Today 5: 76–81). In contrast to the murine system (Nicola, N. A., et al. (1983) J. Biol. Chem. 258: 9017–9021; Ihle, J. N., et al. (1982) J. Immunol. 129: 2431–2436; Fung, M. C., et al. (1984) Nature 307: 233–237; Gough, N. M., et al. (1984) Nature 309: 763–767), human CSFs have been less well characterized, both biologically and biochemically (Nicola, N. A., et al. (1979) Blood 54: 614–627; Wu, M. C., et al. (1980) J. Clin. Invest. 65: 772–775; Golde, D. W., et al. (1980) Proc. Nat'l. acad. Sci. USA 77: 593–596; Lusis, A. J., et al. (1981) Blood 57: 13–21; Abboud, C. N., et al. (1981) Blood 58: 1148–1154; Okabe, T., et al. (1982) J. Cell. Phys. 110: 43–49). Purification to apparent homogeneity has only been reported for macrophage active CSF (CSF-1) (Das, S. K., et al. (1981) Blood 58: 630–641; Das, S. K., et al. (1982) J. Biol. Chem. 257: 13679–13684) and erythroid potentiating activity [Westbrook, C. A. et al. J. Biol. Chem. 259: 9992–9996 (1984)] and for granulocyte-macrophage CSF (GM-CSF) [Gasson, J. C., et al. Science 226: 1339–1342 (1984)], but not for human pluripotent CSF.

Assays are available to detect human clonogenic precursors that give rise to cells of the erythroid, granulocytic, megakaryocytic, macrophage (CFU-GEMM) (Fauser, A. A., et al. (1978) Blood 52: 1243–1248; Fauser, A. A., et al. (1979) Blood 53: 1023–1027) and possibly lymphoid (Messner, H. A., et al. (1981) Blood 58: 402–405) lineages. CSFs with activities on these multipotential progenitor cells (pluripotent CSF or P-CSF) are produced by nitogen- or antigen activated T lymphocytes (Ruppert, S., et al. (1983) Exp. Hematol. 11: 154–161) and constitutively by human tumor cell lines such as the SK-HEP-1 human hepatoma cell line (J. Gabrilove, K. Welte, Li Lu, H. Castro-Malaspina, M. A. S. Moore, Blood, in Press and hereby incorporated by reference); the 5637 bladder carcinoma cell line (reported herein and in Proc. Nat'l. Acad. Sci. 82: 1526–1530 1985 hereby incorporated by reference); and by the HTLV-transformed lymphold cells (Fauser, A. A., et al. (1981) Stem Cells 1: 73–80; Salahuddin, S. Z., et al. (1984) Science 223: 703–707). Pluripotent CSF is involved in the proliferation and differentiation of pluripotent progenitor cells leading to the production of all major blood cell types. This is therefore a broad spectum CSF. It also induces differentiation of leukemic cells.

SUMMARY

This application concerns human puripotent colony stimulating factor CSF for the stimulation of proliferation and differentiation of pluripotent progenitor cells to all major blood cell types which is purified to apparent homogeneity. Its biological effects include the induction of functional markers of differentiation of normal and leukemic cells.

BRIEF DESCRIPTION OF THE DRAWINGS

FIG. 4 shows SDS-PAGE whereas

DESCRIPTION

Figure 1:
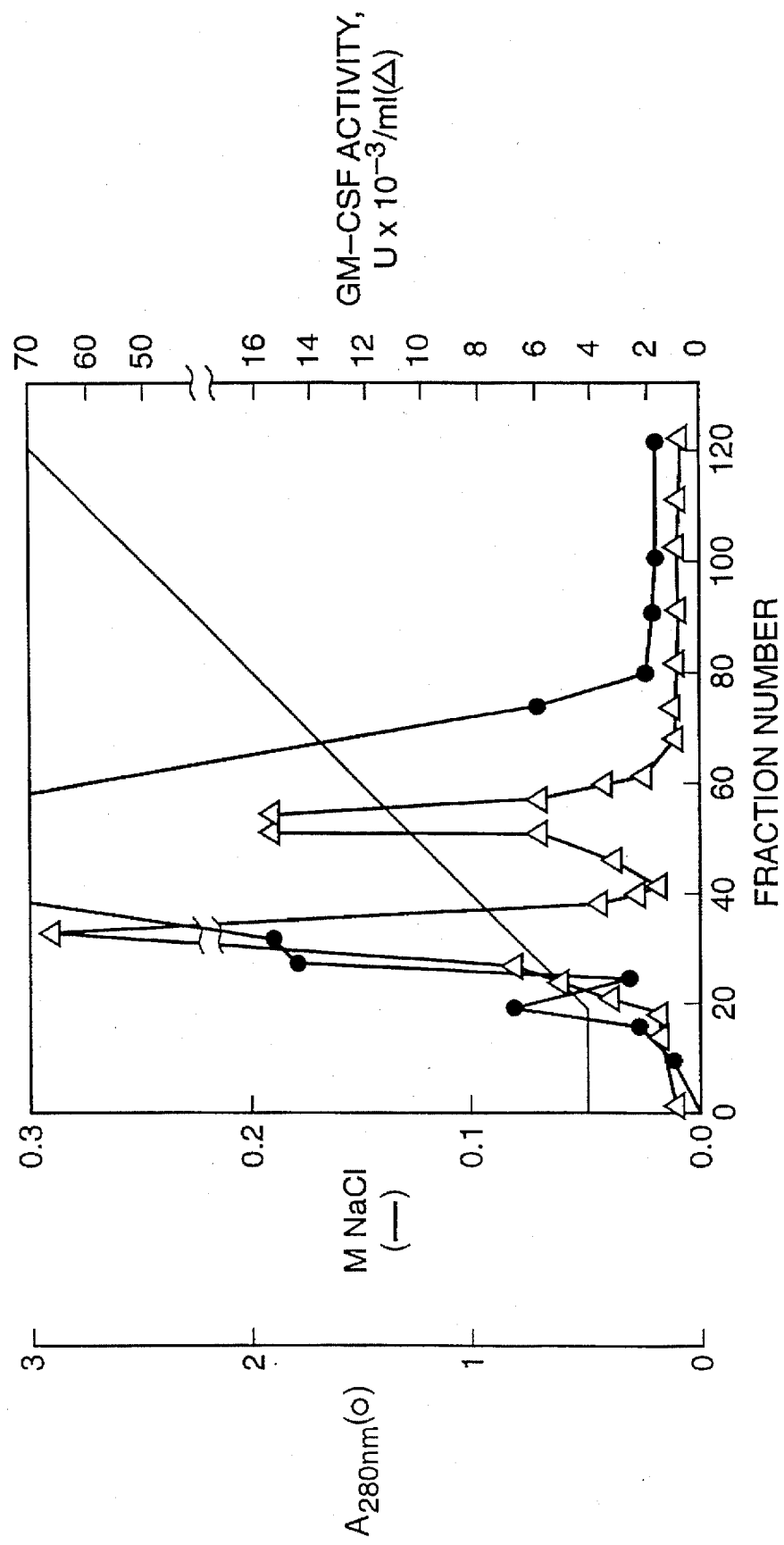
FIG. 1 shows ion-exchange chromatography of 5637 conditioned medium (CM) followed by the Gel filtration chromatograph shown in FIG. 2.

Description of the Drawings FIG. 1: Ion exchange chromatography

One liter dialyzed ammonium sulfate-precipitate of 5637 CM was applied in 0.05M Tris/Hcl, pH 7.8, on a 1 L DEAE cellulose (DE 52) column. Bound proteins were eluted with a linear gradient of NaCl (0.05–0.3M) in 0.05M Tris/Hcl, pH 7.8, as indicated (–). The elution of proteins was monitored by absorption at 280 nm (e—e) and each fraction was tested for CSF activities (GM-CSF activity: Δ). Proteins from the first peak of GM-CSF activity eluted from the column gave rise to mixed colonies in a CFU-GEMM assay and were used for further purification (pluripotent CSF).

Figure 2:
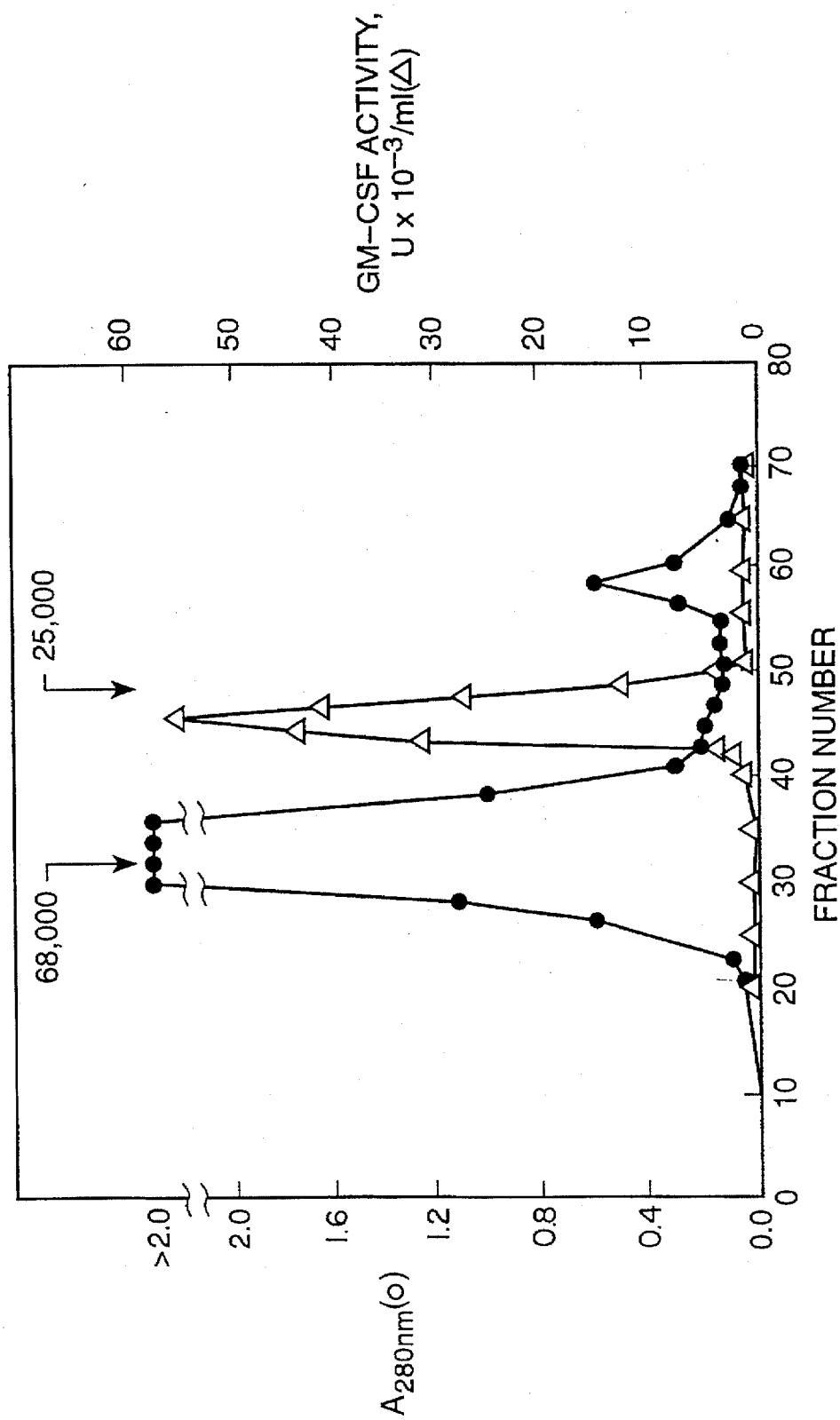

FIG. 2: Gel filtration chromatography

The pluripotent CSF containing concentrated pool of DEAE cellulose chromatography was loaded on an AcA 54 Ultrogel column (2.6×90 cm) and eluted with PBS. Arrows denote the slution points of bovine serum albumin (MW 68,000), and chymotrypsinogen (MW 25,000). The elution of proteins was monitored by absorption at 280 n/n (e—e) and each fraction was tested for pluripotent CSF activity (GM-CSF activity: Δ).

Figure 3:
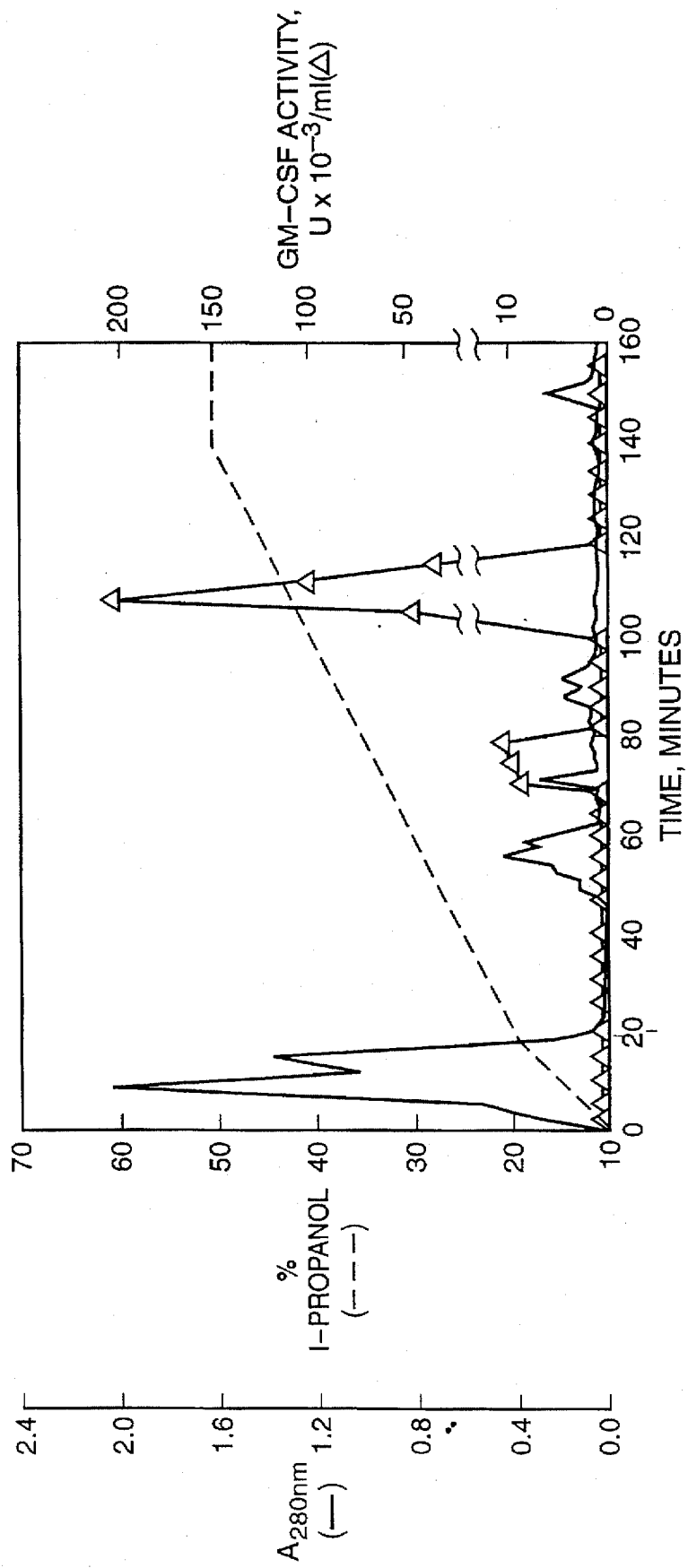
FIG. 3 shows pooled gel filtration eluants on HPLC (reverse phase).

FIG. 3: Reverse phase high-performance liquid chromatography (HPLC)

The pooled fractions with pluripotent CSF activities eluted from the gel filtration cole were acidified to pH 4.0 and loaded onto a C 18 (uBondapak, Waters) column. The bound proteins were eluted with a linear gradient of 1-propanol in 0.9M acetic acid/0.2M pyridine, pH 4.0. The slution of proteins were monitored by absorption at 280 nm (–) and each fraction was tested for pluripotent CSF activity (GM-CSF activity: Δ).

Figure 4:
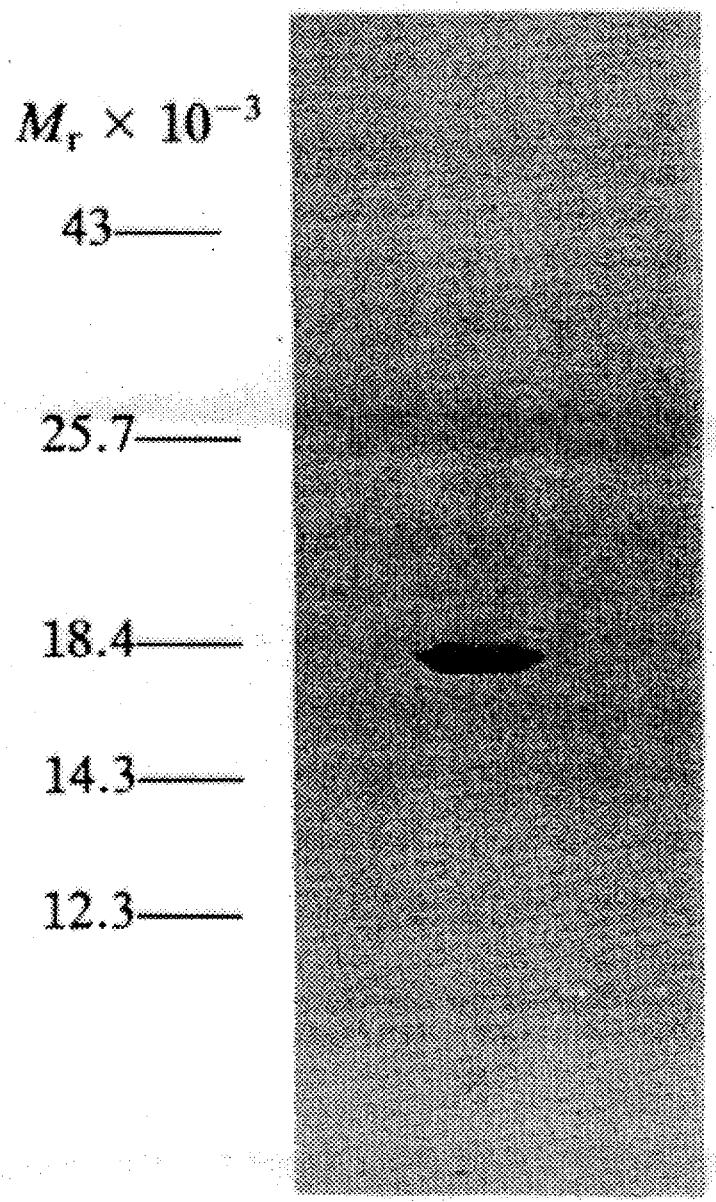

FIG. 4: SDS-polyacrylamide gel electrophoresis (SDS-PAGE)

The pluripotent CSF eluted from the HPLC column (200 ng; peak fraction) was lyophilized and treated with 1% SDS in 0.0625M Tris/HCl, pH 6.8, and 20% glycerol, under reducing conditions (5% 2-mercaptoethanol) for one hour at 37° C. and then applied to a 15% polyacrylamide gel. After electrophoresis, the protein bands were visualized by the silver staining technique.

Figure 5:
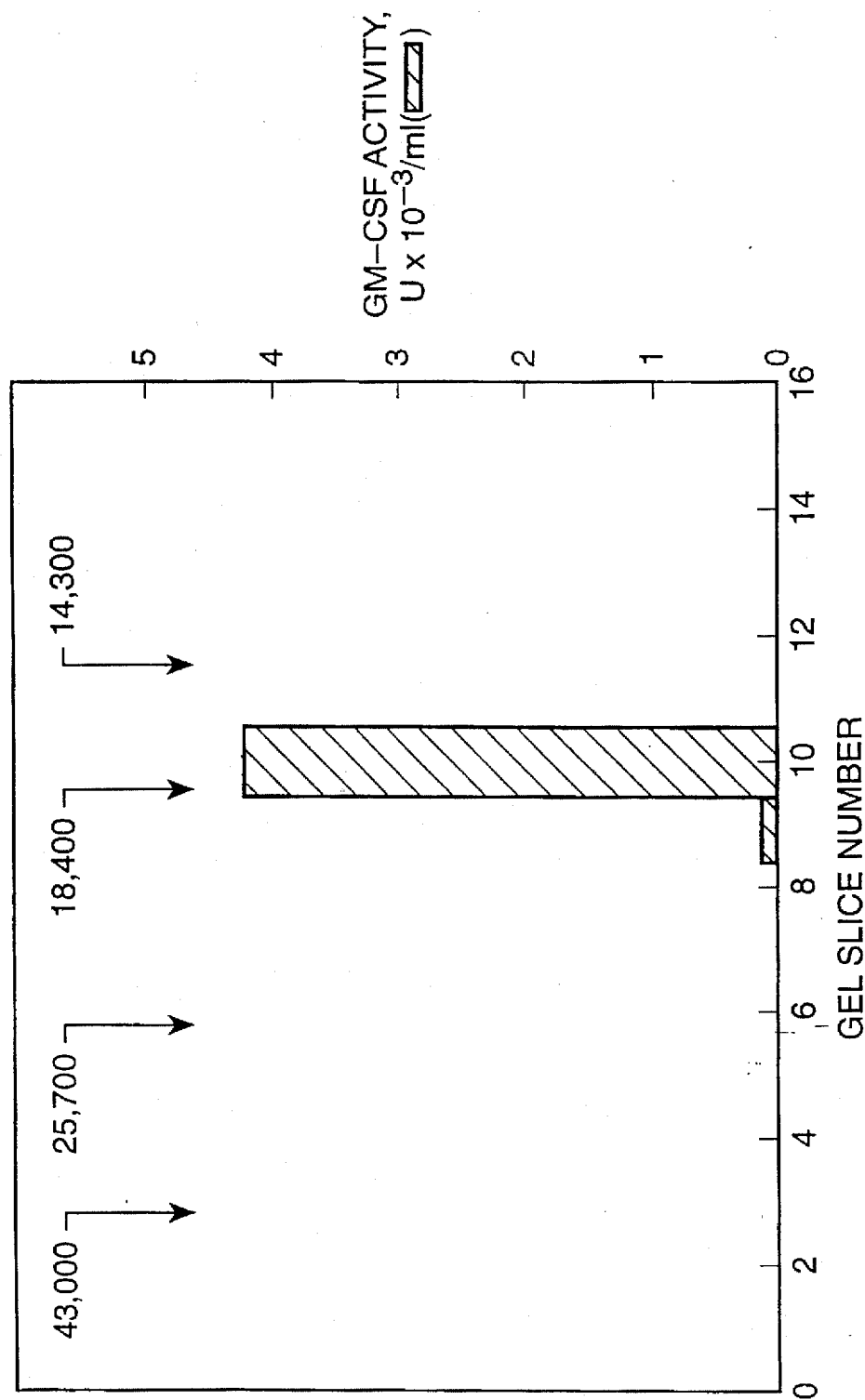
FIG. 5 shows preparative SDS-PAGE and FIG. 6 isoelectrofocusing of the purified pluripotent CSF.

FIG. 5: Preparative SDS-PAGE

Pluripotent CSF eluted from HPLC (FIG. 3) was treated and processed (under non-reducing conditions) as shown in FIG. 4. After electrophoresis, the gel was sliced into 4 mm sections and proteins from each slice were eluted into RPMI 1640 containing 10% FCS. After 18 hours, eluted-proteins were assayed for pluripotent CSF activity (GM-CSF activity: shaded area).

Figure 6:
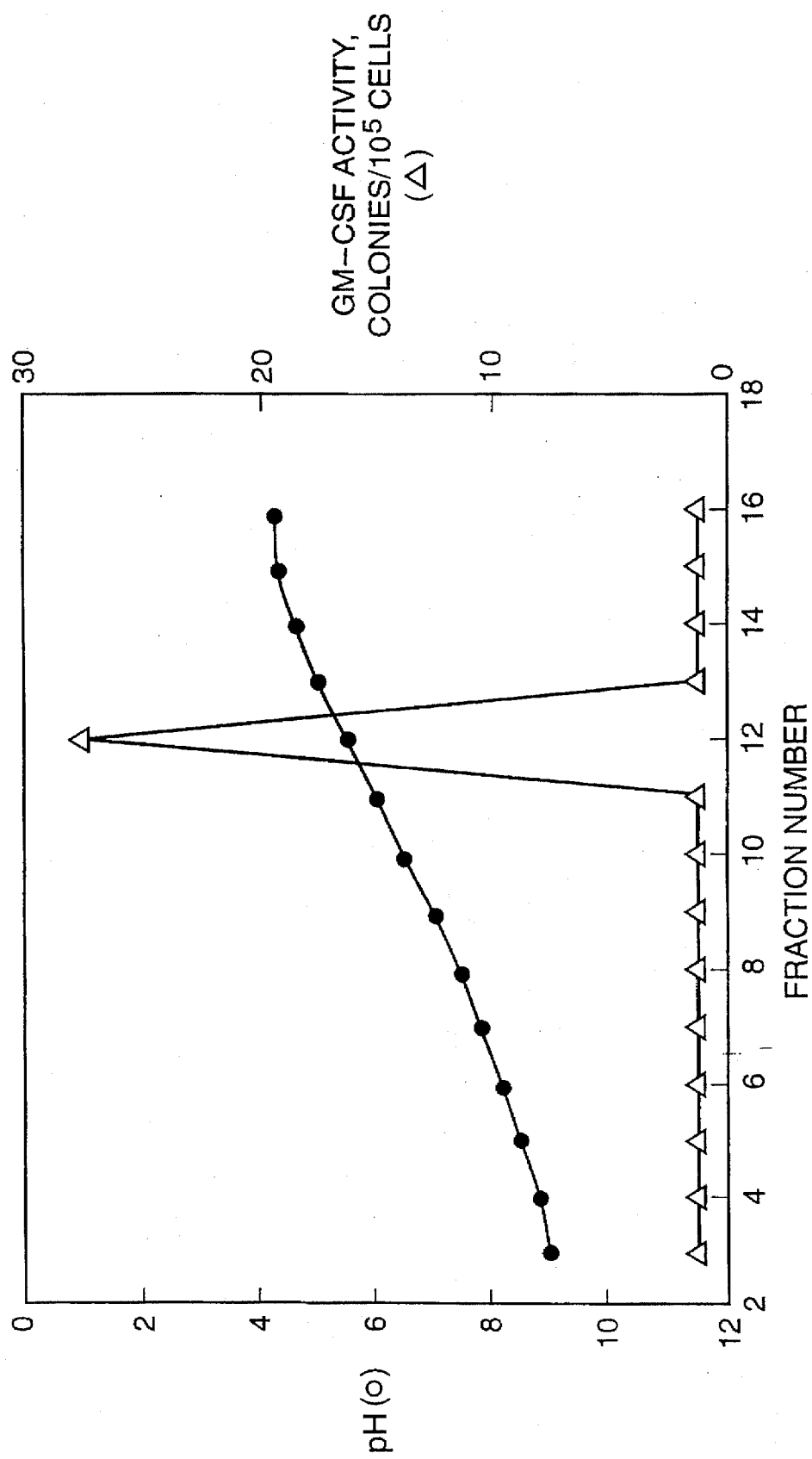

FIG. 6: Isoelectrofocusing

HPLC purified lyophilized pluripotent CSF was supplemented with 20% (v/v) glycerol and 2% ampholines (pH 3.5–10) and layered onto the isodense region of an 0–60% gradient of glycerol containing 2% ampholines (pH 3.5–10). After isoelectrofocusing (2,000 V, 24 hours), 5 ml fractions were collected and the pH (o) determined in each fraction. All fractions were subsequently dialyzed and tested for pluripotent CSF activity (GM-CSF activity: Δ).

We report the purification and biochemical characterization of a human pluripotent CSF, produced and released constitutively by human cells especially tumor cells such as bladder carcinoma cell line 5637 (ATCC HTB-9) and hepatoma cell line SK-HEP-1 (ATCC HTB52). The cell line (5637) was obtained from Jorgen Fogh at Sloan-Kettering Institute, 1275 York Avenue, New York, N.Y. 10021.

Pluripotent CSF biological properties include differentiation of progenitor cells to all major blood types as well as differentiation of leukemic cells.

Assay for GM-CSF Activity

GM-CSF activity was tested on human bone marrow (BM) cells cultured with serial dilutions of test samples in semi-solid agar. BM from healthy human volunteers, who gave informed consent, was diluted 1:5 in phosphate buffered saline (PBS) and separated by density gradient centrifugation on Ficoll-Hypaque. $10^5$ separated cells were plated in 1 ml of 0.3% agar culture medium that included supplemented McCoy's 5A medium and 10% heat inactivated fetal calf serum (FCS), as described (Broxmeyer, H. E., et al. (1977) Exp. Hematol. 5: 87–102). To this mixture serial dilutions of a laboratory standard or test samples (10%; v/v) in RPMI 1640 with 10% FCS were added. Cultures were scored for colonies (greater than 40 cells/aggregate) and morphology was assessed after 7 and 14 days of incubation. GM-CSF units were determined from dose response curves and expressed as U/ml, where 50 U is the CSF concentration stimulating half-maximal colony number to develop (Nicola, N. A., et al. (1983) J. Biol. Chem. 258: 9017–9021).

Assay for Colony Stimulating Factor for BFU-E and CFU-GEMM

The colony assay for human BFU-E and CFU-GEMM was performed as previously described (Li Lu, et al. (1983) Blood 61: 250–256). Human bone marrow cells were subjected to a density cut with Ficoll-Hypaque (density 1.077 gm/cm$^3$; Pharmacia Fine Chemicals, Piscataway, N.J.) and the low density cells were suspended in RPMI 1640 containing 10% FCS at $2\times10^7$ cells/ml and placed for adherence on Falcon tissue cultures dishes (#3003, Becton Dickinson and Co., Cockeysville, Md.) for 1½ hr. at 37° C. The nonadherent cells were depleted of T lymphocytes by rosetting with neuraminidase-treated sheep erythrocytes. Medium conditioned by leukocytes from patients with hemochromatosis in the presence of 1% (v/v) phytohemagglutinin (PHA) (Li Lu, et al. (1983) Supra) as positive control or serial dilutions of test samples were then added at 5% (v/v) to $5\times10^4$ of these low density, non-adherent and T lymphocyte depleted bone marrow cells in a 1 ml mixture of Iscove's modified Dulbecco medium (GIBCO Grand Island, N.Y.), 0.8% methylcellulose, 30% FCS, $5\times10^{-5}$M 2-mercaptoethanol, 0.2 mM Hemin, and one unit of erythropoietin (Ryclone, or Connaught Labs., Willowdale, Ontario, Canada). The addition of Hemin is necessary to obtain optimal cloning efficiency (Li Lu, et al. (1983) Exp. Hematol. 11: 721–729). Dishes were incubated in a humified atmosphere of 5% $CO_2$ in air at 37° C. After 14 days of incubation, colonies were scored and morphology was assessed.

As shown above, a single protein stimulates colony formation by CFU-GEMM, BFU-E, and CFU-GM progenitor cells. This protein we termed "pluripotent CSF". Due to the low numbers of mixed colonies per dish attainable in this assay system, titration of test samples for determination of pluripotent CSF activity meets with considerable difficulties. Therefore, we used the GM-CSF assay units as described above to measure the GM-CSF aspect of the pluripotent CSF activity in those samples that supported growth of BFU-E and CFU-GEMM for calculating the specific activity throughout the purification procedure.

Differentiation Induction Assay

Titrated samples of purified pluripotent CSF were assayed for differentiation induction of WEHI 3B (D+) or HL-60 leukemic cells as described (Metcalf, D. (1980) Int. J. Cancer 25: 225–233; Fibach, E., et al., J. Cell Physiol. 113: (1) 152 (1982)).

Rossette Assays for Fc Receptor, OKM1 and Leu M2 antigens

Cell receptors for immunoglobulin Fc were assayed with IgG (Cappel Laboratories, West Chester, Pa.) coated sheep erythrocytes as described elsewhere (Ralph, P., et al. (1983) Blood 62: 1169). OKM1 (Ortho Diagnostics Systems Inc., Raritan, N.J.) or Leu M2 (Beckton Dickinson, Mountain View, Calif.) reactive antigens were detected by incubating $10^6$ cells/0.1 ml phosphate buffered saline containing 1.0 ug/ml monoclonal antibody for 20 min at 24° C., washing, incubating 20 min at 24° C. with a a: 100 dilution of rabbit anti-rat (Leu M2) or anti-mouse (OKM1) IgG serum (Cappel Laboratories, Cochranville, Pa.), washing and rosetting with protein A-coated erythrocytes as described previously (Ralph, P. et al., Supra).

Assays for fMLP Receptor

Receptors for chemotactic peptide, formyl-Methionyl-Leucyl-Phenylalanine (fMLP), were assayed as follows; $2\times10^6$ cells were incubated with 15 nM $^3$H-fMLP (New England Nuclear, Boston, Mass.) in a total volume of 0.2 ml in the presence or absence of 10 uM unlabelled fMLP (Sigma Corp, St. Luis, Mont.). After three hrs at 4° C. the cell suspensions were rapidly filtered onto glass fiber dies (Whatman Inc., Clifton, N.J.), which were then washed with 30 mls of 4° C. phosphate buffered saline (Harris, P. et al. (1985) Cancer Res. 45: 9). Radioactivity on the discs were counted by liquid scintillation spectrophotometry.

Measurement of PMA-Stimulated Hydrogen Peroxide Release

The production of hydrogen peroxide in response to PMA stimulation was assayed by horse radish peroxidase (HRPO)

(Sigma) mediated $H_2O_2$ dependant oxidation of homovanillic acid (HVA) (Sigma), as described (Harris, et al. Supra (1985). Briefly, cells ($1\times10^6$) were suspended in 2 ml of a solution containing 100 micromolar HVA, 5 U/ml HRPO in the absence or presence of 30 ng/ml PMA. Following 90 min incubation at 37° C., the incubation was centrifuged and 0.25 ml of 25 mM EDTA, 0.1M glycine-NaOH, pH 12 was added to the supernates. A 30% stock solution of hydrogen peroxide (Sigma) was used to prepare $H_2O_2$ standards (0.001 to 50 Moles/assay) for the construction of a standard curve. The HVA oxidation product was measured on a Perkins-Elmer Model MPF-44A fluorescence spectrophotometer. Excitation and emission were set at 312 nm and 420 nm, respectively.

Prostaglandin Measurements

Cells for prostaglandin production assay were washed three times in phosphate-buffered saline and placed in fresh RPMI 1640 media (without FCS) in the presence or absence of 10 micrograms/ml Concanvalin—A (Con-A). Cells were cultured for 24 hrs, centrifuged and the supernates harvested. Supernates were stored at −20° C. until assayed.

Prostaglandin standards $PGE_2$, 6-keto-$PGFl_a$ and $TBX_2$ were kindly supplied by by Dr. J. Pike (Upjohn Company, Kalamazzo, Mich). Tritium labelled compounds were purchased from New England Nuclear (Boston, Mass.). Rabbit antisera to $PGE_2$ were obtained from the Pasteur Institute (Paris, France). Antibodies to 6-keto $PGFl_a$ were raised in the laboratory (Rashida Karmali). The cross reactivity of these antibodies for the non-targeted PGs were to greater than 4% except for the $PGE_2$ antisera which cross reacted 10% with $PGE_1$ standard. The procedure for extracting the prostaglandins has been described earlier (Karmali, R. A., et al. (1982) Prostagl. Leukotr. Med. 8: 565). Briefly, a trace of [$^3$H]-PG was added to aliquots of standard and samples before being extracted once with petroleum ether. After acidification to pH 3.5, the samples were extracted twice with diethyl ether, dried under nitrogen and reconstitution in assay buffer. The efficiency of this extraction procedure to this point was 85–95%. Standard quantities of each prostaglandin (0–1000 pg) or the extracted sample to be measured were prepared in 0.1 ml aliquots of assay buffer. Antisera and label were added succesively in 0.1 ml aliquots and incubated at 4° C. for 8–12 hours. Bound and free [$^3$H]-PG were separated by 0.5 ml dextran-coated charcoal (0.5–1.0% w/v) to estimate the amount of each compound in the unknown sample. The detection limit of this assay has been found to be 10 pg. The intra-assay coefficient of variation was 9.0%.

Alkaline and Acid Phosphatase, b-Glucuronidase and N-Acetyl Glucuronidase Assays Cell extracts were prepared in 0.5 ml of PBS 1% NP-40, incubated 5 min at 24° C., then spun for 10 min. at $3\times10^4$ g. Supernates were collected and assayed. Extracts were assayed of their alkaline and acid phosphatase, b-glucuronidase and N-acetyl glucuronidase activity using the respective Sigma kits. Activities of extracts are expressed as change in absorbance per unit time per unit sample volume divided by the cell concentration in the culture or in the extract and compared to control activity. Measurements were made in a Beckman ACTA-CV spectrophotometer.

Glycoconjugate assay

Cytokine preparations were assayed in a [$^3$H]-Glucosamine incorporation assay. Replicate wells were plated with 100 microliters of inducing agent to be tested. Previously washed (3× in PBS) HL-60 or U937 cells ($1\times10^7$ cells/ml) in RPMI 1640 without FCS were added (50 microliters). After a four hour incubation 20 microliter 25 uCi/ml [$^3$M]-Glucosamine in 1% BSA (w/v) in PBS was added to the culture and plates were incubated for an additional 16 hours. Cells were harvested (Mini-Mash, Microbiological Associates, Md.) onto glass filter paper with water wash (×4, 0.1 ml each), followed by 0.4N Perchlorate wash (×4, 0.1 ml) and water (2×, 0.1 ml). Radioactivity on glass discs was determined by liquid scintillation spectrophotometry.

Statistical Analysis

Student's T test to compare means was carried out using the significance limits of a two tailed test.

Preparation of 5637 cell line conditioned medium (5637 CM)

The human bladder carcinoma cell line 5637 has been reported to produce a colony stimulating factor for granulocytes and macrophages (Svet-Moldavsky, G. J., et al. (1980) Exp. Hematol. 8 (Suppl. 7): 76). The cell line has been maintained at Sloan-Kettering Institute (New York, N.Y.) for several years. It is serially passaged by trypsinization in the presence of EDTA and grows rapidly to form an adherent monolayer in plastic tissue culture flasks. Routinely, cells are cultured in RPMI 1640, supplemented with 2 mM L-glutamine, antibiotics and 10% FCS. For purification of pluripotent CSF activity from 5637 conditioned medium (5637 CM), confluent cell cultures were intermittently cultured in medium containing 0.2% FCS. After 48–72 hours, 5637 CM was harvested, cells and cell debris removed by centrifugation (20 min, 10,000×g), and stored at −20° C. until use.

5637 cells also contain a multitude of subclones which either produce p-CSF in better yield and/or have less inhibitor present. Over 120 subclones have been isolated. One such subclone 1A6 was found to produce at least twice as much as the parent cell line and possibly 5–10 fold more resulting in a range of between 2–10 times more p-CSF from the 1A6 subclone than from the parent 5637 cell line as as determined by the assay methods outlined. This subclone or the parent cell line 5637 can be used to isolate p-CSF in good yield. Subclones are isolated by limiting single dilution techniques to produce a single cell per well in order to grow up a pure cell line from each well. Best results are obtained if the cells are distributed such that 37% of the wells (one out of every three) show growth at a certain dilution. There is then a good mathematical chance of obtaining subcloning to obtain outgrowth of only one cell from the one of three wells showing growth. Subclone 1A6 cell line is on deposit and available at Sloan-Kettering Institute for Cancer Research 1275 York Avenue, New York, N.Y. 10021. We refer to use of the 1A6 in a U.S. patent application Ser. No. 768,959 filed Aug. 23, 1985 entitled "Production of Pluripotent Granulocyte colony-stimulating Factor" by Lawrence M. Souza to yield sequence data on the protein p-CSF with subsequent preparation of recombinant p-CSF from such a sequenced probe (P11–top P14) as follows:

(B) Sequencing of Materials Provided by Revised Methods

In order to obtain a sufficient amount of pure material to perform suitably definitive amino acid sequence analysis, cells of a bladder carcinoma cell line 5637 (subclone 1A6) as produced at Sloan-Kettering were obtained from Dr. E. Platzer. Cells were initially cultured Iscove's medium (GIBCO, Grand Island, N.Y.) in flasks to confluence. When confluent, the cultures were trypsinized and seeded into roller bottles (1½ flasks/bottle) each containing 25 ml of preconditioned Iscove's medium under 5% $CO_2$. The cells were grown overnight at 37° C. at 0.3 rpm.

Cytodex-1 beads (Pharmacia, Uppsala, Sweden) were washed and sterilized using the following procedures. Eight grams of beads were introduced into a bottle and 400 ml of PBS was added. Beads were suspended by swirling gently for 3 hours. After allowing the beads to settle, the PBS was drawn off, the beads were rinsed in PBS and fresh PBS was added. The beads were autoclaved for 15 minutes. Prior to use, the beads were washed in Iscove's medium plus 10% fetal calf serum (FCS) before adding fresh medium plus 10% FCS to obtain treated beads.

After removing all but 30 ml of the medium from each roller bottle, 30 ml of fresh medium plus 10% FCS and 40 ml of treated beads were added to the bottles. The bottles were gassed with 5% $CO_2$ and all bubbles were removed by suction. The bottles were placed in roller racks at 3 rpm for ½ hour before reducing the speed to 0.3 rpm. After 3 hours, an additional flask was trypsinized and added to each roller bottle containing beads.

At 40% to 50% of confluence the roller bottle cultures were washed with 50 ml PBS and rolled for 10 min. before removing the PBS. The cells were cultured for 48 hours in medium A [Iscove's medium containing 0.2% FCS, $10^{-8}$M hydrocortisone, 2 mM glutamine, 100 units/ml penicillin, and 100 ug/ml streptomycin]. Next, the culture supernatant was harvested by centrifugation at 3000 rpm for 15 min., and stored at −70° C. The cultures were refed with medium A containing 10% FCS and were cultured for 48 hours. After discarding the medium, the cells were washed with PBS as above and cultured for 48 hours in medium A. The supernatant was again harvested and treated as previously described.

Approximately 30 liters of medium conditioned by 1A6 cells were concentrated to about 2 liters on a Millipore Pellicon unit equipped with 2 cassettes having 10,000 M.W. cutoffs at a filtrate rate of about 200 ml/min. and at a retentate rate of about 1000 ml/min. The concentrate was diafiltered with about 10 liters of 50 mM Tris (pH 7.8) using the same apparatus and some flow rates. The diafiltered concentrate was loaded at 40 ml/min. onto a 1 liter DE cellulose column equilibrated in 50 mM Tris (pH 7.8). After loading, the column was washed at the same rate with 1 liter of 50 mM Tris (pH 7.8) and then with 2 liters of 50 mM Tris (pH 7.8) with 50 mM NaCl. The column was then sequentially eluted with six 1 liter solutions of 50mM Tris (pH 7.5) containing the following concentrations of NaCl: 75 mM; 100 mM; 125 mM; 150 mM; 100 mM; and 300 mM. Fractions (50 ml) were collected, and active fractions were pooled and concentrated to 65 ml on an Amicon ultrafiltration stirred cell unit equipped with a YM5 membrane. This concentrate was loaded onto a 2 liter AcA54 gel filtration column equilibrated in PBS. The column was run at 80 ml/hr. and 10 ml fractions were collected. Active fractions were pooled and loaded directly onto a C4 high performance liquid chromatography (HPLC) column.

Samples, ranging in volume from 125 ml to 850 ml and containing 1–8 mg of protein, about 10% of which was hpG-CSF. Samples were loaded onto the column at a flow rate ranging from 1 ml to 4 ml per minute. After loading and an initial washing with 0.1M ammonium acetate (pH 6.0–7.0) in 80% 2-propanol at a flow rate of 1/ml/min. One milliliter fractions were collected and monitored for proteins at 220 nm, 260 nm and 280 nm.

As a result of purification, fractions containing hpG-CSF were clearly separated (as fractions 72 and 73 of 80) from other protein-containing fractions. HpG-CSF was isolated (150–300µ) at a purity of about 85±5% and at a yield of about 50%. From this purified material 9 µg was used in Run #4, an amino acid sequence analysis wherein the protein sample was applied to a TFA-activated glass fiber disc without polybrene. Sequence analysis was carried out with an AB 470A sequencer according to the methods of Hewick, et al., *J. Biol. Chem.*, 256, 7990–7997 (1981) and Lai, *Anal. Chem. Acta.* 163, 243–248 (1984). The results of Run #4 appear in Table III.

TABLE III

```
1                    5                         10
Thr—Pro—Leu—Gly—Pro—Ala—Ser—Ser—Leu—Pro—
                  15                             20
Gln—Ser—Phe—Leu—Leu—Lys—(Lys)—Leu—(Glu)—Glu—
                  25                             30
Val—Arg—Lys—Ile—(Gln)—Gly—Val—Gly—Ala—Ala—
Leu—X—X
```

In Run #4, beyond 31 cycles (corresponding to residue 31 in Table III, no further significant sequence information was obtained. In order to obtain a longer unambiguous sequence, in a Run #5, 14 µg of hpG-CSF purified from conditioned medium were reduced with 10 µl of -mercaptoethanol for one hour at 45° C., then thoroughly dried under a vacuum. The protein residue was then redissolved in 5% formic acid before being applied to a polybrenized glass fiber disc. Sequence analysis was carried out as for Run #4 above. The results of Run #5 are given in Table IV.

TABLE IV

```
1                    5                         10
Thr—Pro—Leu—Gly—Pro—Ala—Ser—Ser—Leu—Pro—Gln—
                  15                             20
Ser—Phe—Leu—Leu—Lys—Cys—Leu—Glu—Gln—Val—Arg—
                  25                             30
Lys—Ile—Gln—Gly—Asp—Gly—Ala—Ala—Leu—Gln—Phe—
                  35                             40
Lys—Leu—Gly—Ala—Thr—Tyr—Lys—Val—Phe—Ser—Thr—
                  45
(Arg)—(Phe)—(Met)—X—
```

The amino acid sequence give in Table IV was sufficiently long (44 residues) and unambiguous to construct probes for obtaining hpG-CSF cDNA as described infra." (end quote).

Ammonium Sulfate Precipitation, Ion-exchange-chromatography, Gel filtration

The first three purification steps (($NH_4)_2SO_4$-precipitation, Ion-exchange-chromatography on DEAE cellulose, DE 52, Whatman, Clifton, N.J., and gel filtration on AcA 54 Ultrogel, LKB, Inc. Rockland, Md.) were performed as described (Welte, K., et al. (1982) J. Exp. Med. 156: 454–464) except that AcA 54 was used instead of AcA 44 (see also Descriptions of FIGS. 1 and 2).

Reverse Phase High-Performance Liquid Chromatography (RP-HPLC)

RP-HPLC was performed with a Waters HPLC system (M 6,000 solvent delivery pumps, model 400 variable wavelength detector, data module and data processor, Waters, Associates, Milford, Mass.). The separation was performed on a uBondapak C18 column (Waters). The buffers used were: Buffer A: 0.9M acetic acid/0.2M pyridine, pH 4.0; buffer B: buffer A in 50% 1-propanol (Burdick and Jackson, Lab., Muskegon, Mich.). Acetic acid and pyridine were purchased from Fisher, Scientific Co. The pluripotent CSF containing pool obtained from gel filtration was acidified with acetic acid to pH 4.0 and injected onto the uBondapak C18 column without regard to sample volume. The column was washed with buffer A (10 min) and bound proteins were eluted using a steep gradient 0–40% buffer B within the first 20 min and a 40–100% gradient of buffer B in 120 min. The flow rate was adjusted to 1 ml/min and 3 ml fractions were collected. From each fraction a 0.5 ml aliquot was supplemented with 10% FCS, dialyzed against PBS and tested for pluripotent CSF activity.

Isoelectrofocusing

One ml of the purified pluripotent CSF was supplemented with 20% glycerol (vol/vol) and 2% Ampholines (vol/vol), pH 3.5–10 (LKB Products, Inc.). A 5–60% glycerol density gradient containing 2% Ampholines, pH 3.5–10, was layered into a isoelectrofocusing column (LKB 8100). The pluripotent CSF sample was applied onto the isodense region of the gradient, followed by isoelectrofocusing (2,000 V, 24 hours). Five ml fractions were collected and the pH determined in each fraction. The fractions were dialyzed against PBS and subsequently tested for pluripotent CSF activity.

Sodium Dodecylsulfate-Polyacrylamide Gel Electrophoresis (SDS-PAGE)

The discontinuous Tris-glycine system of Laemmli (Laemmli, U.K. (1970) Nature 227: 680–685) was used for 1.5 mm slab gels of 15% acrylamide. The samples (200 ng lyophilized protein eluted from HPLC) were treated with 1% SDS in 0.0625M Tris-HCl, pH 6.8 at 37° C. for 1 hour under both reducing (5% 2-mercaptoethanol) and non-reducing conditions and then loaded on the gel. After electrophoresis, gels were stained by the Biorad silver staining method (Biorad Laboratories, Rockville Centre, N.Y.). Apparent molecular weights were determined using protein standards ovalbumin (MW 43,000), chymotrypsinogen (MW 25,700), beta-lactoglobulin (MW 18,400), lysozyme (MW 14,300) and cytochrome C (MW 12,300) (Bethesda Research Laboratories, Inc. Gaithersburg, Md.) or from Pharmacia Fine Chemicals, Piscataway, N.J. After treatment (see above) of lyophilized pluripotent CSF under non-reduced conditions and subsequent electrophoresis, parallel gels were sliced in 4 mm or 2 mm sections, respectively and proteins from each slice eluted either into 0.5 ml RPMI 1640 containing 10% FCS or into phosphate buffered saline (PBS; 20 mM phosphate, 0.15M NaCl). After extensive dialysis, the eluted material was assayed for pluripotent CSF activity.

Protein Assay

The protein content of samples were measured using the Lowry technique (Lowry, O. H., et al. (1951) J. Biol Chem. 193: 265–275). For protein concentrations lower than 2 microgram/ml, samples were subjected to SDS-PAGE, the protein bands were visualized by the silver staining technique and the protein concentration estimated by comparison with a serial dilution of known amounts of proteins.

The examples shown serve to illustrate the invention without limiting same.

EXAMPLE I

Pluripotent CSF activity in 5637 CM

Confluent layers of 5637 human bladder carcinoma cells, when cultured for 48–72 hours in the presence of 10% FCS, released into the culture medium 3,000–10,000 units/ml of GM-CSF activity. Media conditioned in the presence of 0.2% FCS still contained 10–30% of this activity, whereas in serum free 5637 CM the activity drops below 5% of the activity obtained in the presence of 10% FCS. Although GM-CSF activity in 5637 CM is readily detectable in soft agar bone marrow cultures, not all batches of unfractionated 5637 CM support in vitro growth of BFU-E and CFU-GEMM. Four to ten times concentrated 5637 CM support in vitro growth of BFU-E and CFU-GEMM. Four to ten times concentrated 5637 CM reduced colony formation by CFU-GM 30–70% indicating the presence of inhibitor(s) in 5637 CM. Inhibitors were removed after ion-exchange chromatography.

EXAMPLE II

Purification of pluripotent CSF

A 20-fold concentration of proteins from the 5637 CM was achieved by precipitation with ammonium sulfate at 80% saturation. The dialyzed precipitate was loaded on to a DEAE cellulose (DE 52) column. Bound proteins were eluted with a salt gradient from 0.05–0.3M NaCl in 0.05M Tris-HCl, pH 7.8. GM-CSF activity eluted as peak 1 between 0.075M and 0.1M NaCl and with a second peak at 0.13M NaCl (FIG. 1). Since only peak 1 revealed pluripotent CSF activity, was used only this pool for further purifications. Peak 2 included proteins with only GM-CSF activity. We calculated the "fold" purification by measuring the GM-CSF activity of pluripotent CSF. In the unfractionated CM we could not discriminate between GM-CSF activity as part of pluripotent CSF activity and GM-CSF activity without pluripotent properties. Therefore we considered the GM-CSF activity contained in peak 1 from DE 52 as the starting activity (Table 1).

Since in the subsequent purification schedule GM-CSF, BFU-E and CFU-GEMM activities copurified in all steps, we named these combined activities "pluripotent CSF" and have used this term thereafter. The proteins of peak 1 of DE 52 chromatography (including pluripotent CSF activity) were concentrated by dialyzing against 50% (w/v) Polyethylenglycol in PBS and purified further by ACA 54 Ultrogel gel filtration. The pluripotent CSF activity eluted in fractions 42–49 as a single peak corresponding to a molecular weight of 32,000 daltons (FIG. 2). This step resulted in a 65% recovery of activities and a 15 fold increase of specific activities (Table 1).

The final step involved chromatography on a reverse phase HPLC column (uBondapak C 18). The majority of proteins did not bind to this column or eluted at low 1-propanol concentrations (less than 20% 1-propanol; FIG. 3). A minor peak of GM-CSF activity without activity in the CFU-GEMM and BFU-E assays but differentation inducing activity on HL-60 leukemic cells was eluted at around 30% 1-propanol. Pluripotent CSF activity eluted as a single sharp peak at 42 % 1-propanol (FIG. 3). This purification step resulted in a 600-fold increase of specific activity and a 25% recovery of activity. The protein content of the HPLC fraction was measured by comparing the density in silver stained SDS-PAGE with protein standards of known concentrations. Using this measurement, we obtained a specific activity of $1.5 \times 10^8$ U/mg protein and a final purification of 9,000-fold, calculated from the first peak of DEAE cellulose chromatography. The overall yield was 6.2%. The purification table with the degree of purification of pluripotent CSF as measured by GM-CSF activity, protein content, specific activity and yield is detailed in Table 1.

The final preparation obtained after HPLC (pluripotent CSF activity peak fraction) was analyzed on a 15% SDS-PAGE gel followed by the sensitive silver staining technique (FIG. 4). Only one major protein band with a molecular weight of 18,000 was seen under both, reducing (5% 2-mercaptoethanol) (FIG. 4) and non-reducing conditions.

Since the buffer system used for HPLC did not allow monitoring the protein elution pattern by measuring the optical density at 280 nm, we applied proteins of all active fractions on SDS-PAGE. The density of the stained protein band at 18,000 MW in the peak and side fractions was proportional to the amount of biological pluripotent CSF activity. After electrophoresis under non-reducing conditions, a parallel gel was sliced into 4 mm sections and proteins eluted from each slice into RPMI 1640 containing 5% FCS. Pluripotent CSF activity was found to be localized in the slice number corresponding to 18,000 MW (FIG. 5).

In three additional, independent purification runs, pluripotent CSF had the same properties and specific activity as described above. In all three runs parallel gels were sliced into 2 mm sections, proteins eluted into PBS and tested for pluripotent CSF activity. Re-electrophoresis of the proteins eluted from the slices with pluripotent CSF activity agains revealed one single band in a silver stained gel with a molecular weight of 18,000, identical to that shown in FIG. 4.

However further work using markers from Pharmacia shows the molecular weight of the glycosylated p-CSF to be 19,600. The unglycosylated recombinant protein shows a M.W. of 18,800.

The purified CSF was also subjected to isoelectrofocusing analysis using a 5–60% glycerol gradient in an IEF column and 2% Ampholines, pH 3.5–10. Pluripotent CSF activity was localized in one fraction (5 ml) with an isoelectric point of 5.5 (FIG. 6). The total recovery of pluripotent CSF activity applied to the column was approximately 20%.

Pluripotent CSF activity did not bind to a Concanavalin A agarose. Treatment with neuraminidase did not abolish the biological activity and did not change the IEP. However, the isoelectrofocusing under our conditions did not allow judgment of minor changes of the IEP. These findings suggest that glycosylation might not be a major structural feature.

The partial amino acid sequence was determined by Applied Molecular Genetics (Thousand Oaks, Calif.) on an AB 1470A- Beatrice microsequencer. From the amino terminal end the sequence is Threo, Pro, Leu, Gly, Pro, Ala, Ser, Ser, Leu, Pro. Also see the extended 44 residue sequence above.

EXAMPLE III

Biological activity of pluripotent CSF: Progenitor cell stimulation and Effect on Leukemic cells.

1. Progenitor cells:

Fifty unit of GM-CSF activity, enough to support the half maximal growth of CFU-GM, had no clear effect in a, CFU-GEMM assay; however, 500 U/ml (GM-CSF activity) of pluripotent CSF clearly supported the growth of human mixed colonies (CFU-GEMM), megakaryocytic colonies, and early erythroid colonies (BFU-E) under our experimental conditions (Table IIA & IIB).

Pluripotent-CSF supports the growth of colony forming progenitors of the granulocyte, mixed granulocyte, macrophage, eosinophil and megakaryocytic cell types. These results can be seen for example in vitro.

We show the results of comparison of 5637-CM and 1A6-CM in Table IIC at dilutions of 1/10 through 1/1600. The 1/10 dilution of 1A6 shows an inhibitor to be present in the CM. Essentially this table serves as an example that the 1A6 subclone of 5637 has 8.7 times more p-CSF in U/ml under growing conditions containing FCS.

When purifying p-CSF the FCS is reduced to 0.2%.

2. Pluripotent CSF also induces the differentiation of leukemic cells. For example, leukemic cell lines HL-60 and WEHI-3B (D+) are induced to differentiate along the granulocytic and/or macrophage pathway. The human leukemic cell line KG-1 responds to pluripotent CSF by increased colony formation in agar and proliferation in liquid suspension culture.

As for mature cells pluripotent CSF induces increased protein content, for example, in macrophages, whereas IL-3 is not reported to be active on macrophages. (Table III). 50 U/ml and 200 U/ml of GM-CSF activity of the pluripotent CSF were needed to induce half-maximal differentiation of the leukemic cell lines WEHI-3B(D+) and HL-60, respectively. These cells were used in a test system (Metcalf Int. J. Cancer (1980) 25: 225 and Fibach et al. (1982) 113: 152) Table IV(A&B) to show the effect of pluripotent-CSF on leukemic cells. U937 was obtained from Dr. Nilsson and HL-60 from DR. Gallo as freeze-backs of early passages. HL-60 is a myeloid cell line from an acute promyelocytic leukemia [Gallagher et al. Blood 54: 713 (1979)]. U937 is a histiocytic lymphoma cell line (Sundstrom and Nilsson (1976) Int. J. Cancer 17: 565).

Differentiation of leukemic cells lines in vitro can be achieved by a variety of nonphysiologic (e.g. DMSO, phorboldiesters) and physiologic (e.g. retinoic acid, vitamin $D_3$) inducers (Koeffler et al. (1983) Blood 62: 709). Murine G-CSF is known to be a potent inducer of differentiation of WEHI-3B (D+) murine myelomonocytic leukemia cells, whereas Interleukin 3 lacks this activity (Nicola et al. (1984) Immunol. Today 5: 76) (See Table V).

Pluripotent-CSF was tested for leukemia differentiating activity (GM-DF) in a clonal assay system described by Metcalf ((1980) Int. J. Cancer 25: 225; Fibach, E., et al. J. Cell. Physiol. Supra) using murine WEHI-3B (D+) and human HL-60 promyelocytic leukemia cell lines (Platzer et al. (in press) (1985). Quantitation of GM-DF was obtained by incubation of leukemic cells in agar with serial dilutions of pluripotent CSF. Pluripotent CSF had GM-DF activity on both cell lines. However, HL-60 required approximately 2.5–5× higher concentrations of Pluripotent CSF to achieve 50% differentiated, spreading colonies versus undifferentiated tight blast cell colonies, than did WEHI-3B (D+) (Platzer et al. 1985, Supra).

Morphological and cytochemical analysis of HL-60 colonies were performed using alpha-naphthylacetate esterase (ANAE) and luxol fast blue (LFB) stains, as markers of the monocyte, macrophage and eosinophil granulocyte lineage respectively (Platzer, E., et al. J. Immunol. in press). In the presence of pluripotent CSF there is observed an increase in the number of colonies containing polymorphonuclear cells (by hematoxylin stain), LFB$^+$ cells and in intensity of ANAE stain. Therefore pluripotent CSF induces differentiation along the macrophage as well as granulocyte pathway. The human leukemia cell line KG1 (courtesy Dr. H. P. Koeffler) responded to Pluripotent CSF in a dose dependent manner with increased colony formation in agar and increased $^3$M-thymidine incorporation after 24–48 hrs. in suspension culture. This might indicate that the GM-DF activity of Pluripotent CSF reflects the differentiating capacity of a given leukemic cell lines rather than an intrinsic property of the factor.

CM from SK-HEP and cell line 5637 containing pluripotent CSF (free of Interferon) has also shown acquisition of immunoglobulin Fc receptor, growth inhibition, increased expression of monocyte related surface antigens and an increase in lysosomal enzyme content as well as (to distinguish P-CSF from Interferon-gamma) increased receptors for chemotactic peptide, increased hydrogen peroxide release in response to phorbol myristic acetate (PMA) stimulation and the release of prostaglandins (PGE$_2$ and 6-keto PGF$_{1A}$) as features of differentiation of human promyelocytic leukemia cell line HL-60 and monoblastic leukemia cell line U937. These broad range differentation factors are thus different from Interferon and conventional-colony stimulating activity (CSA) (Harris et al. submitted). Highly purified pluripotent CSF increased the receptors for chemotactic peptide and increased glycoconjugate synthesis as a feature of differentiation in both the human promyelocytic leukemia cell line HL-60 and monoblastic leukemic cell line U937.

3. Pluripoietin CSF shows species crossreactivity on normal murine bone marrow and leukemic cells:

Normal mouse bone marrow cells cultured in agar for 7 days in the presence of saturating concentrations of Pluripoietin formed approximately 10% of the colonies supported by WEHI-3B conditioned media as standard source of CSF('s). All colonies formed in the presence of Pluripotent CSF were of similar morphology,. not staining for alpha-naphthyl-acetate esterase or Kaplow's myeloperoxidase; this suggests that a subpopulation of murine colony forming progenitors is responsive to Pluripotent CSF. Weak cross species activity was found on continuous murine mast cell lines, established as described from murine long-term bone marrow cultures (Tertian et al. (1980) J. Immunol. 127: 788). 5,000 cells/well of a mast cell growth factor (MCGF) dependent murine mast cell line were incubated for 24 hrs. at 37° C. in 96 well plates with serial dilutions of growth factors, and then assayed for $^3$H-thymidine uptake as described (Yung et al. (1981) J. Immunol. 127: 794). Results demonstrate little more than 10% murine MCGF activity of Pluripotent CSF as compared to ConA-LBRMCM, which was used as a standard preparation of murine MCGF. The murine Interleukin 3 dependent cell line FDC-P2 (courtesy Dr. M. Dexter) did not respond with increased $^3$H-thymidine uptake to concentrations of Pluripoietin as high as 2,000 U/ml.

We herein describe the purification of a pluripotent CSF, which is constitutively produced by the human bladder carcinoma cell line 5637, its 1A6 subclone or SK-HeP-1. This protein is capable of stimulating the in vitro growth of mixed colony progenitor cells (CFU-GEMM), early erythroid progenitor cells (BFU-E), megakaryocytic (CFU-Mega), granulocyte-macrophoage progenitors (CFU-GM) and in addition induces differentiation of both the murine myelomoncytic (WEHI-3B(D+)) and the human promyelocytic (HL-60) leukemic cell lines (E. Platzer, K. Welte, J. Gabrilove, Li Lu, M. A. S. Moore, manuscript in preparation). The purified pluripotent CSF had a specific activity in the GM-CSF assay of 1.5×10$^8$ U/mg protein. To our knowledge this is the highest specific activity for a human pluripotent CSF reported to date. Pluripotent CSF has a molecular weight of 32,000 by gel filtration and 18,000 by SDS-PAGE under both, reduced and non-reduced conditions and an isoelectric point of 5.5. Pluripotent CSF activities could be eluted from gel slices representing the same molecular weight range as the stained protein band.

The purified protein shown in SDS-PAGE is consistent with pluripotent CSF because: 1) The profile of protein elution visualized in SDS-PAGE and elution of pluripotent CSF activity (FIG. 3) from reverse phase HPLC columns is equivalent in the major fraction and side fractions; 2) additional chromatography of the purified protein on diphenyl or octyl reverse phase HPLC columns using acetonitrile or ethanol as organic solvents for elution did not lead to a separation of protein and pluripotent CSF activity; 3) identical localization of protein band and pluripotent CSF activity in a preparative SDS-PAGE; 4) high specific GM-CSF activity (1.5×10$^8$ U/mg protein). Since purified pluripotent CSF is apparently homogeneous, amino acid sequence analysis of the purified protein has been initiated and is partially determined.

Based on the molecular weight of pluripotent CSF as 18,000 it could be calculated that 1 U of pluripotent CSF was equivalent to 6.7 pg protein or 3.7×10$^{-16}$ moles. A pluripotent CSF concentration of 50 U/ml or 1.85×10$^{-11}$M was required for half maximal colony formation form CFU-GM activity in normal human bone marrow cells.

A ten-fold increase in the amount of pluripotent CSF (500 U/ml GM-CSF activity) was required for clear detection of human CFU-GEMM and erythroid BFU-E activities (Table II); a 1–2 or 1–2.5 fold increase in pluripotent CSF (e.g. 50×200 U GM-CSF) was needed to induce the differentiation of either WEHI-3 B (D+ or HL-60 leukemic cells, respectively. These data suggest that the particular action(s) of pluripotent CSF are determined by its concentration as first suggested by Burgess and Metcalf (Blood, Supra) in the murine system. The fact, that human pluripotent CSF is able to induce differentiation of leukemic cell lines makes it a protein with unique properties, since for the murine multi CSF (Interleukin 3) no differentiation activity on leukemic cells has been reported (Ihle, J. N., et al. (1982) J. Immunol. 129: 2431–2436; Nicola, et al. (1984) Immunol. Today 5: 76, Watson, et al. (1983) Immunol. Today 5: 76, and Fung et al. (1984) Nature 307: 233). (Table V compares the two entities). The murine IL-3 dependent cell line FDC-P2 (Dr. M. Dexter) did not respond with increased $^3$H-thymidine uptake to Pluripotent-CSF as high as 2,000 U/ml.

Several human CSFs (GM-CSF, G-CSF, eosinophilic CSF, erythroid potentiating activity) have molecular weights between 30,000 and 40,000 on gel filtration (Nicola, N. A., et al. (1979) Blood 54: 614–627; Golde, D. W., et al. (1980) Proc. Nat'l. Acad. Sci. USA 77: 593–596; Lusis, A. J., et al. 1981) Blood 57: 13–21; Abboud, C. N., et al. (1981) Blood 58: 1148–1154; Okabe, T., et al. (1982) J. Cell. Phys. 110: 43–49) which is similar to the native molecular weight of the pluripotent CSF described here. However, only partially purified erythroid-potentiating activity has been reported to have activity in a CFU-GEMM assay (Fauser, A. A., et al. (1981) Stem Cells 1: 73–80).

Constitutive production of pluripotent CSF by the bladder carcinoma cell line 5637 and its 1A6 subclone or other 5637 subclones suggests that these are valuable source for large scale production and for isolation and cloning of the gene which codes for pluripotent CSF. The availability of purified human pluripotent CSF has important and far reaching implications in the management of clinical diseases involving hematopoietic derangement or failure, either alone or in combination with other lymphokines or chemotherapy. Such disorders include leukemia and white cell disorders in general. It is useful in transplantation, whether allogeneic or autologous, to augment growth of bone marrow progenitor cells. It can be used in induced forms of bone marrow aplasia or myelosuppresion, in radiation therapy or chemotherapy-induced bone marrow depletion, wound healing, burn patients, and in bacterial inflammation. Here the action of pluripotent-CSF may possibly be due to enhancement of chemotactic peptide receptors or by functioning as a chemoattractant. It is also found in saliva so may prevent tooth decay and oral infection.

p-CSF may be used alone or together with recombinant material or in conjunction with erythropoietin for treatment in hematopoietic disorders.

TABLE I

Purification of human pluripotent CSF

| Fraction | Protein | Total activity[a] (U × 10$^{-6}$) | Specific activity (U/mg) | Purification (fold) | Yield (%) |
|---|---|---|---|---|---|
| 5637 CM | 2 g | 12 | 6 × 10$^3$ | — | 100 |
| DEAE-cellulose | 300 mg | 5 | 1.7 × 10$^4$ | 1[b] | 42 |
| AcA 54 Ultrogel | 13 mg | 3.1 | 2.4 × 10$^5$ | 14 | 26 |
| RP-HPLC | 5 μg | 0.74 | 1.5 × 10$^6$ | 9,000 | 6.2 |

[a]GM-CSF activity of pluripotent CSF; U = Units
[b]estimate of fold purification based on starting activity of peak 1 of DEAE cellulose chromatography

TABLE IIA

A Comparison of CFU-GEMM and BFU-E activities of pluripotent CSF (500 U/ml GM-CSF activity)

| Experiment # | CFU-GEMM[a] (Colonies ± 1 SEM) | | | BFU-E[a] (Colonies ± SEM) | | |
|---|---|---|---|---|---|---|
| | 1 | 2 | 3 | 1 | 2 | 3 |
| Medium | 0.3 ± 0.3 | 0 | 0 | 42 ± 6 | 17 ± 3 | 17 ± 2 |
| PHA-LCM[b] | 7 ± 1 | 3 ± 0 | 3.3 ± 0.3 | 67 ± 1 | 65 ± 3 | 34 ± 3 |
| Pluripotent CSF | 7.7 ± 2.1 | 4 ± 0.8 | 2.3 ± 0.9 | 85 ± 6 | 31 ± 1 | 28 ± 2 |

[a]Target cells were 5 × 10$^4$/ml low density, non-adherent and T cell depleted normal human bone marrow cells. Experiment 3 was done in the absence of Hemin.
[b]Medium conditioned by leukocytes from patients with hemochromatosis in the presence of 1% PHA. (positive control)

TABLE IIB

Activity of Pluripoietin on pre-CFU

| Pluripoietin concentration | Exp. 1 7 days in suspension culture | Exp. 2 7 days in suspension culture | Exp. 3 5 days in suspension culture | Exp. 3 9 days in suspension culture |
|---|---|---|---|---|
| 1000 U/ml | 416 ± 18 | 20 ± 4 | 32 ± 5 | 80 ± 8 |
| 500 U/ml | 367 ± 57 | 39 ± 4 | n.t. | n.t. |
| 100 U/ml | n.t. | 29 ± 6 | 73 ± 4 | 30 ± 5 |
| 10 U/ml | n.t. | 12 ± 3 | 52 ± 3 | 34 ± 4 |
| Control medium | 200 ± 16 | 8 ± 2 | 26 ± 5 | 20 ± 4 |

TABLE IIC

COMPARISON OF ACTIVITY OF 5637 AND 1A6 IN GM CFU ASSAY

| Cells | 1/10 | 1/100 | 1/200 | 1/400 | 1/800 | 1/16000 | U/ml |
|---|---|---|---|---|---|---|---|
| Colonies 5637-CM | 190 ± 17 | 75 ± 1 | 18 ± 6 | 0 | 0 | 0 | 2750 ± 350 |
| % | 100% (max) | 39% of max. | 9% | | | | |
| Colonies 1A6 | 0 ± 0 | 93 ± 7 | 130 ± 11 | 124 ± 0 | 64 ± 0 | 30 ± 6 | 24,000 ± 3,000 |
| % | 0% | 49 | 69 | 65 | 34 | 16 | |

Legend Table II

Normal human bone marrow cells were separated by Ficoll, adherence to plastic and depletion of T cells by rosetting with neuraminidase treated sheep red blood cells, as described (Platzer, E., et al. J. Immunol./in press). Quadruplicate cultures of 25,000 cells in 100 microliters/well were incubated in 96 well flat bottom tissue culture plates in Iscove's modified Dulbecco's medium supplemented with 30% fetal bovine serum (FBS), 5×10$^{-5}$M 2-mercaptoethanol and serial dilutions of purified Pluripoietin or control medium for 5, 7 or 9 days at 37° C. in 5% $CO_2$ in air. Contents of each well were then resuspended and incorporated into i ml agar system in supplemented McCoy's with saturating concentrations (10% v/v) of 5637 CM, as described (Platzer, E., et al. 1985 Supra, Welte, K., et al. (1985) Proc. Nat'l. Acad. Sci. U.S.A. in press). Colonies were scored after 7 days of incubation at 37° C. in a humidified atmosphere of 5% $CO_2$ in air. Results are expressed as mean colony number per well ±1 standard deviation. CFU input on day 0 were 79±5 (exp. 1), 26±1 (exp. 2) and 22±3 (exp. 3) per well. Bone marrow cells from the donor for experiment 1 grew high numbers of CFU-GM in two unrelated experiments; no pathophysiological situation was recognized.

TABLE III

Influence of Pluripoietin on protein content in cultures of human macrophages

| Time in culture | Adherent cell protein in response to control medium μg/coverslip | Adherent cell protein in response to Pluripoietin μg/coverslip |
|---|---|---|
| Day 1-2 | 10.0 ± 2.0 | 28.6 ± 7.7 |
| Day 1-3 | 20.4 ± 1.6 | 26.8 ± 2.5 |
| Day 1-4 | 28.4 ± 1.6 | 41.2 ± 1.9 |
| Day 4-5 | 28.8 ± 1.6 | 28.1 ± 3.6 |
| Day 4-6 | 43.1 ± 4.7 | 28.1 ± 3.6 |
| Day 4-7 | 38.2 ± 6.1 | 44.8 ± 0.7 |

Legend Table III

Normal human monocytes/macrophages were isolated from peripheral blood mononuclear cells by adherence to glass surfaces [25]. Two×10$^6$ cells were plated per 13 mm diameter coverslips in 0.1 ml of supplemented RPMI 1640 containing 25% fresh frozen human serum. After 2 hrs. at 37° C., nonadherent cells were removed by rinsing, and coverslips transferred to 24 well tissue culture trays (day 0). On day 1 and 4, supernatants were replaced by fresh culture medium containing 500 U/ml of purified Pluripoietin or control medium. Protein content was determined 1 to 3 days thereafter by rinsing coverslips free of culture medium, solubilizing adherent cell protein in 0.5N NaOH and measuring protein concentration according to the method of Lowry.* Results are expressed as mean ±1 standard deviation, from triplicate cultures.

*Lowry et al., J. Biol. Chem., Supra

TABLE IVA

Leukemia differentiating (GM-DF) activity of purified Pluripoietin

| Puri-fication | GM-CSF activity Specific activity U/mg protein | GM-DF activity WEHI-3B (D+) U/ml | | GM-DF activity HL-60 U/ml | |
|---|---|---|---|---|---|
| | | U/ml | Ratio DF/CSF | U/ml | Ratio DF/CSF |
| I | $1.5 \times 10^8$ | 84,000 | 246,000 | 2.9 | 54,000 | 0.6 |
| II | $1.25 \times 10^8$ | 201,000 | 502,000 | 2.5 | 80,000 | 0.4 |

TABLE IVB

Glycoconjugate Synthesis

| Inducer | HL-60 CPM/5 × $10^5$ cells | U937 |
|---|---|---|
| media | 465 | 210 |
| gIFN 500 U/ml | 1029a | 1500a |
| 300 U/ml | 800a | 537a |
| 50 U/ml | 410 | 258 |
| LK 50% | | |
| (500 U/ml gIFN) 5637 CM (CM-CSA) | 427 | 910a |
| 2 kU/ml | 1828a | 1200a |
| 1 kU/ml | 980a | 780a |
| 500 U/ml | 670a | 490a |
| fluripoetin[b] 1KU | 4235a | 2400a |
| pp aCSF[c] 1KU | 430 | 306 |
| SK-Hep Cm 50% | 1439a | 604a |
| GCT-CM 100% | 420 | 200 |
| PMA 3.0 ng/ml | 490a | 250 |
| 50.0 ng/ml | 2000a | 1700a |
| aIFN 5000 U/ml | 420 | 240 |
| IL-2 100 U/ml | 425 | 230 |

*Significantly different from control, p less than 0.05 by Students T test.
[b]Human P-CSF, units assigned by CFU activity.
[c]partially purified aCSF-like activity, units assigned by $CFU_c$ activity.

Glycoconjugate synthesis was measured as follows, cells ($5 \times 10^5$) were incubated with inducers for 4 hrs then glucosamine incorporation was evaluated after an additional 16 hr.

Results are mean values from three or more experiments a. Significantly different from control, p less than 0.05 by Students T test. b. Human P-CSF, units assigned by $CFU_c$ activity. c. partially purified mCSF-like activity, units assigned by $CFT_c$ activity.

Legent Table IVA

For determination of specific activity, protein concentration of purified Pluripoietin was estimated by comparison with serial dilutions of known amounts of protein in SDS-PAGE, visualized by silver stain. Due to the low frequency of CFU-GEMM in normal human bone marrow cells, the biological activity of Pluripoietin had to be measured using the GM-CSF assay. We compared the ability of serial dilutions of Pluripoietin and a previously determined laboratory standard of 5637 CM to support GM-colony formation in 1 ml semi-solid agar cultures containing $10^5$ low density, normal human bone marrow cells. Fifty units of GM-CSF activity were arbitrarily defined as inducing 50% of maximal colony growth on day 7 of culture. Concentrations of 500 U/ml of Pluripoietin were sufficient to stimulate colony growth from CFU-GEMM and BFU-E comparable to that supported by optimal amounts of phytohemagglutinin-activated lymphocyte conditioned media. Two independent purifications (I and II) resulted in very similar specific activity. Due to different amounts of starting material, the final concentration of biological activity differs between I and II, but is useful for comparison of GM-CSF and leukemia differentiating activity (GM-DF) of Pluripoietin. GM-DF activity was determined by incubating $3 \times 10^2$/ml WEHI-3B(D+) or $10^3$/ml HL-60 leukemic cells in 0.31 agar in McCoy'medium containing 12.5% FBS with serial dilutions of Pluripoietin. Cultures were scored on day 7 (WEHI-3E) and day 14 (HL-60) for induction of disperse, differentiated colonies vs. tight, blast cell colonies (Metcalf, et al., (1980) Int. J. Cancer 25: 225 and Fibach, et al., (1982) J. Cell. Physiol. 113: 152). Fifty units of GM-DF activity were defined as inducing 50% differentiated colonies.

TABLE V

Biological activities of purified human pluripoietin and murine Interleukin 3.

| Activity | Pluripoietin[a] | Interleukin 3[b] |
|---|---|---|
| Clonal growth of hemopoietic progenitors: | | |
| CFU-GEMM | + | + |
| BFU-E | + | + |
| CFU-G,M,GM | + | + |
| CFU-EDS | + | + |
| CFU-MEG | n.t. | + |
| pre-CFU-c (ΔGPA) | + | + |
| stem cell multi-plication (CFU-s) | § | n.t. |
| Species crossreactivity[c] | + | — |
| Leukemia differentiating activity (GM-DF) on: | | |
| WEHI-3B (D+) | + | — |
| HL60 | + | — |
| $^3$H-TdR uptake in cell lines: | | |
| KG1 | + | — |
| FDC-P2 | — | + |
| Murine mast cell lines (MCGF activity) | + | + |
| Histamine production | n.t. | + |
| Protein synthesis of mature macrophages | + | n.t. |
| Induction of 20a SDH | § | + |
| Growth of: | | |
| natural cytotoxic cells | § | + |
| pre-B cell clones | n.t. | + |

[a]Pluripoietin was tested on human target cells, if not noted otherwise.
[b]Interleukin 3 activity an murine target cells, if not noted otherwise. Data derived from literature, except GM-DF and activity ors KG1.
[c]Activity on bone marrow derived colony formation in agar cultures.
§No human test system available
n.t. Not tested

What is claimed:

1. A pharmacological preparation containing isolated and purified human pluripotent colony stimulating factor comprising the following characteristics:
   a) a molecular weight of about 19,600 daltons under reducing and non-reducing conditions as determined by SDS-PAGE;
   b) a molecular weight of about 32,000 daltons as determined by gel filtration;
   c) an isoelectric point of about 5.5;

d) the ability to induce differentiation of the leukemia cell line WEHI-3B (D+); and e) the ability to stimulate growth of both human and mouse bone marrow cells.

2. The pharmacological preparation of claim 1, wherein the factor is purified to homogeneity.

3. The pharmacological preparation of claim 1, wherein the factor is isolated from human cells.

4. The pharmacological preparation of claim 1, wherein the factor is isolated from human tumor cells.

5. The pharmacological preparation of claim 1, wherein the factor is isolated from human bladder cell line 5637 or hepatoma cell line SK-HEP-1.

6. The pharmacological preparation of claim 1, further characterized by a) having a specific activity of about $1.5 \times 10^8$ U/mg as measured in the GM-CSF activity assay; and b) having the pharmacological activity to induce differentiation of leukemic cells.

7. The pharmacological preparation of claim 6, wherein the leukemic cells induced are leukemic cell lines.

8. The pharmacological preparation of claim 1 having the ability to induce the acquisition of increased receptors for chemotactic peptide and increased glycoconjugate synthesis.

9. The pharmacological preparation of claim 1, wherein said human pluripotent colony stimulating factor is a glycoprotein isolated from human tumor cells selected from the group consisting of bladder tumor cell line 5637 and hepatoma cell line SK-Hep-1.

10. The pharmacological preparation of claim 9 wherein said human pluripotent colony stimulating factor is prepared by:

a) high-salt precipitation of protein from a cell-free medium;

b) ion exchange chromatography of the precipitate from step a);

c) gel filtration of active fractions from step b); and d) reverse-phase high performance liquid chromatography of active fractions from step c).

* * * * *